May 27, 1975 W. R. HEARD Plant Pat. 3,722
BLACK MAPLE TREE
Filed April 16, 1974
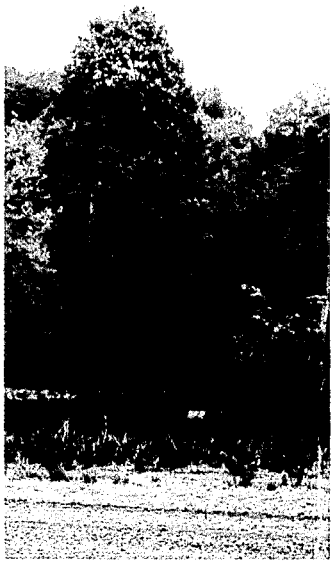
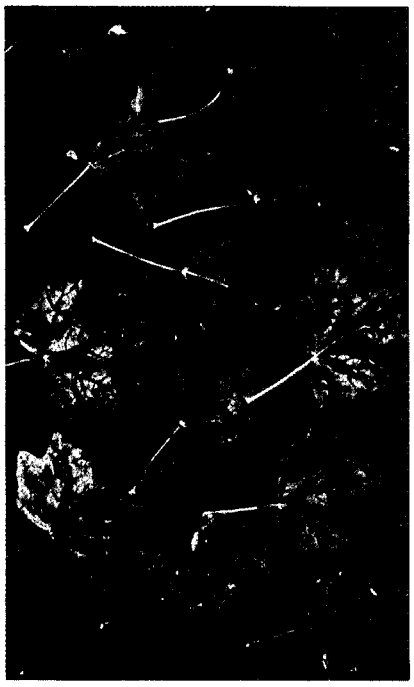
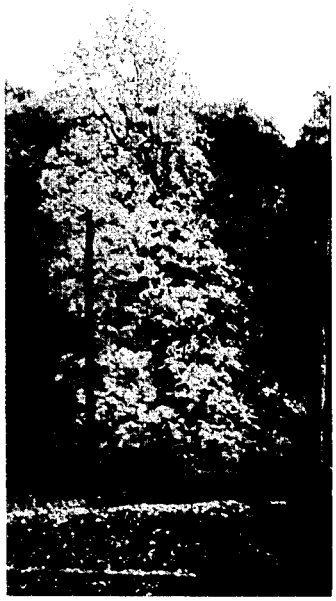
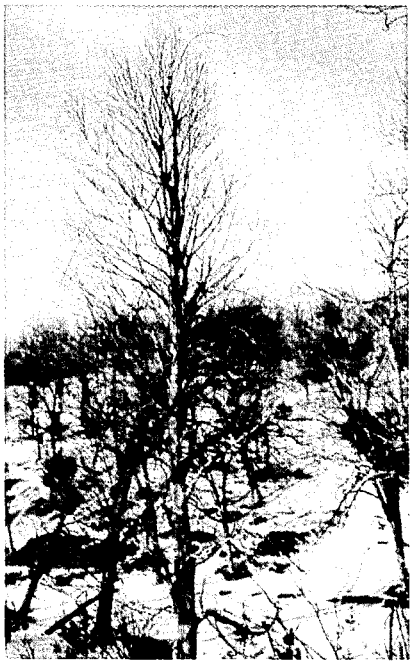

United States Patent

Plant Pat. 3,722
Patented May 27, 1975

1

3,722

BLACK MAPLE TREE

William R. Heard, 5355 Merle Hay Road,
Des Moines, Iowa 50323

Filed Apr. 16, 1974, Ser. No. 461,401
Int. Cl. A01h 5/12
U.S. Cl. Plt—51 1 Claim The present invention relates to a new and distinct variety of black maple tree of the species botanically known as *Acer nigrum*, which was discovered by me as a natural seedling of unknown parentage occurring on cultivated property located in Boone County, Iowa.

While visiting this region in Boone County where the black maple species is native and abounds, my attention was attracted to one particular tree because of its unusual upright and columnar shape which was growing adjacent to a public country road along the edge of a rough woodland pasture. On closer inspection of this tree, I also recognized that its trunk was unusually straight for the black maple species, and its lateral branches were both shorter and thicker than average for the species, while the bark of the trunk was an unusual mottled gray color, as well as warty and alligator-like in appearance. Even when viewed from a distance, the tree was dramatically distinctive and striking because of its shape and form, with very little taper, and terminating at its top in a rounded crown which stood out in sharp contrast to all other black maple trees in the area.

Realizing that such a distinctive black maple tree would be commercially valuable for plantings along narrow city streets and avenues, as well as for screening tree uses and architectural formations, I took budwood from the original mature tree and arranged with a friend to have the same budded onto *Acer saccharum* understock, as performed on my behalf in a tree nursery located at Troutdale, Oreg. Continued observations of both the original tree and those propagated therefrom as aforesaid have convinced me that my new seedling represents a new and improved variety of black maple and fully confirmed that the aforementioned distinctive characteristics thereof come true and are established and transmitted through succeeding propagations.

The accompanying drawing shows a typical mature tree of my new variety during both its green summer foliage and yellow autumn foliage stages, as well as a bare tree specimen, and also shows a close-up view of its typical green summer leaves, all as depicted in color as nearly true as it is reasonably possible to make the same in a color illustration of this character.

The following is a detailed description of my new black maple variety, with color terminology in accordance with Koster's Color Guide, except where general color terms of ordinary dictionary significance are obvious:

Parentage: A natural seedling of unknown parentage.

Propagation: Holds its distinguishing characteristics through succeeding propagations by bud-grafting.

Location where grown and observed: Boone County, Iowa and Troutdale, Oreg.

Tree: Large (from about 65 feet to 70 feet tall and from about 25 to 30 feet wide when fully mature); upright columnar); dense; hardy.

*Trunk.*—Stocky; rough; usually straight for the species. Bark—Warty and alligator-like in appearance. Color—Mottled gray; lighter than normal nearly black color which is typical of the species.

*Branches.*—Stockier and shorter than normal for the species; smooth at first, but becoming rough.

2

Color—Orange-brown at first, but becoming pale, dull gray-brown later. Lenticels—None.

Foliage: Leaves—Abundant; many; dense; alternate and opposite.

*Size.*—Length—From about 3½ inches to 6 inches. Width—From about 3½ inches to 6 inches.

*Shape.*—Mostly 3-lobed but occasionally 5-lobed; blades drooping.

*Color.*—From dull green to rich dark green, ranging from near Holly Green, Plate 82 to near Ivy Green, Plate 83 on upper surface, but more yellowish green and softly downy, especially on yellow veins, on lower surface; color of leaves becomes near Indian Yellow, Plate 8 on upper surface during autumn and slightly lighter yellow on lower surface.

*Margin.*—Lobes acute; entire or obtusely toothed.

*Petiole.*—From medium to long length (usually about 2½ to 3 inches). Color—Varies widely, ranging from deep carmine red in young trees to green in mature trees.

*Glands.*—Normal and typical for the species.

*Stipules.*—None.

Flower buds:

*Hardiness.*—Very hardy throughout a board range of climatic zones from the east and mid-west, to the northwest Pacific coast of the United States.

*Size.*—Small, with dark red-brown scales in winter.

*Shape.*—Acute; often with a pair of side buds.

*Color.*—Exposes bright yellow-green color when opening, as typical of the species.

Flowers: Typical of the species; both male and female flowers sometimes borne in same clusters and sometimes in separate clusters; broadly bell-shaped and 5-lobed, with partly united calyx; have 7 or 8 stamens which are twice as long as the calyx of the male flowers, but much shorter and aborted in the female flower.

Fruit: Usually with wide-spreading wings about ½ inch to 1 inch long.

General observations: While my new variety of black maple tree resembles the species *Acer Nigrum* in many respects, it is distinctly and strikingly different therefrom, particularly in respect to its tall, upright and substantially columnar tree shape which terminates at the top in a rounded crown; and its very straight trunk, with shorter and thicker than normal lateral branches which make the tree especially suitable for narrow street plantings in cities, as well as for screening uses and architectural formations.

I claim:

1. A new and distinct variety of black maple tree of the species botanically known as *Acer nigrum*, substantially as herein shown and described, characterized particularly as to novelty by its very upright, tall and substantially columnar form which terminates at its top in a rounded crown, its very straight trunk which is unusual for the species, with lateral branches which are both shorter and thicker than is normal for the species, by the mottled gray color of the bark of its trunk and which is warty and alligator-like in appearance, and by its dense and attractive foliage which ranges from dull green to rich dark green in color on its upper surface and yellow-green and softly downy, especially on the yellow veins, on its lower surface, said foliage becoming an attractive Indian yellow color on its upper surface and somewhat lighter yellow in color on its lower surface during autumn.

No references cited.

ROBERT E. BAGWILL, Primary Examiner